United States Patent [19]

Cincotta et al.

[11] 4,172,083
[45] Oct. 23, 1979

[54] CARBOCYCLIC ARYL COMPOUNDS SUBSTITUTED WITH A TETRAHYDRO-2H,4H-1,3,6-DIOXAZOCINO MOIETY

[75] Inventors: Louis Cincotta; James W. Foley, both of Andover; Marcis M. Kampe, Brookline, all of Mass.

[73] Assignee: Polaroid Corporation, Cambridge, Mass.

[21] Appl. No.: 836,066

[22] Filed: Sep. 23, 1977

[51] Int. Cl.$^2$ ............................................ C07D 273/00
[52] U.S. Cl. ...................................... 260/338; 548/207
[58] Field of Search ............................................ 260/338

[56] References Cited
PUBLICATIONS

E. V. Dehmlow et al., Tetrahedron Letters, No. 2, p. 95 (1976).
Sandler et al., Organic Functional Group Preparations, vol. III, (1972), pp. 48–49.

*Primary Examiner*—Norma S. Milestone
*Attorney, Agent, or Firm*—Sybil A. Campbell

[57] ABSTRACT

This invention relates to carbocyclic aryl compounds substituted with a tetrahydro-2H,4H-1,3,6-dioxazocino moiety and to the preparation thereof. These compounds are useful as intermediates in the synthesis of certain 3,3-disubstituted-2,3-dihydrobenz[d]isothiazole-1,1-dioxide dyes which find utility as, for example, photographic optical filter agents and filter agent precursors.

9 Claims, No Drawings

CARBOCYCLIC ARYL COMPOUNDS SUBSTITUTED WITH A TETRAHYDRO-2H,4H-1,3,6-DIOXAZOCINO MOIETY

BACKGROUND OF THE INVENTION

1. Field of the Invention

This invention relates to compounds substituted with a tetrahydro-2H,4H-1,3,6-dioxazocino (i.e., with an N-1,3,6-dioxazocanyl moiety) and to the preparation thereof.

2. Description of the Prior Art

Copending U.S. patent application Ser. No. (836,010) of Stanley M. Bloom, Alan L. Borror and James W. Foley filed concurrently herewith is directed to a method of synthesizing 3,3-disubstituted-2,3-dihydrobenz[d]isothiazole-1,1-dioxides possessing a carbonyl group in the 2-position. Depending upon the carbonyl group and the 3,3 substituents, the products of the synthesis may be employed as pH-sensitive indicator dyes, antihalo dyes or photographic optical filter agents. As disclosed and claimed therein, the method of preparing these compounds comprises reacting a 3-(4'-OP-1'-phenyl/4'-OP-1'-naphthyl)-3-(phenyl/naphthyl)-2,3-dihydrobenz[d]-isothiazole-1,1-dioxide wherein P is a protecting group compatible with organometallic reagents and a carboxylic acid halide in the presence of pyridine to yield the corresponding 2-carbonyl derivative. Optionally, the acylation may be carried out by sequentially reacting the said isothiazole compound with an alkali metal hydride to give the corresponding 2-alkali metal salt followed by reaction with the selected carboxylic acid halide. The acylated compound thus prepared is then treated with acid to remove the protecting group and yield the product.

The 3-(4'-OP-1'-phenyl/4'-OP-1'-naphthyl)-3-(phenyl/naphthyl)-2,3-dihydrobenz[d]isothiazole-1,1-dioxides employed as intermediates in the above method may be synthesized by reacting a 3-(4'-OP-1'-phenyl/4'-OP-1'-naphthyl)benz[d]isothiazole 1,1-dioxide and a phenyllithium or a naphthyllithium reagent as disclosed and claimed in copending U.S. patent application Ser. No. 836,008 of Alan L. Borror, Louis Cincotta, James W. Foley and Marcis M. Kampe filed concurrently herewith. The 3-(4'-OP-1'-phenyl/4'-OP-1'-naphthyl)benz[d]isothiazole-1,1-dioxides, which form the subject matter of copending U.S. patent application Ser. No. 836,024 of Alan L. Borror, Louis Cincotta, Ernest W. Ellis, James W. Foley and Marcis M. Kampe filed concurrently herewith, are prepared by converting a blocked 4-halophenol or a blocked 4-halo-1-naphthol to the corresponding Grignard or lithium reagent and then reacting this reagent with saccharin, a saccharin salt or saccharin psuedo-chloride.

As discussed in the aforementioned applications, protecting groups, such as, methoxymethyl and 2-tetrahydropyranyl are useful in preparing the blocked phenols and blocked 1-naphthols, and in addition to protecting the functional hydroxy group, are useful for protecting other hydroxy groups that may be present. For example, such groups may be used to protect an $-N(CH_2CH_2OH)_2$ substituent.

In compounds, such as, $HO(CH_2)_2OH$ and $HO(CH_2)_3OH$, other means for protecting the hydroxy groups also have been employed. In one such method, the 1,2- or 1,3-alkanediol is reacted with formaldehyde in the presence of acid to give the corresponding ring-closed compound,

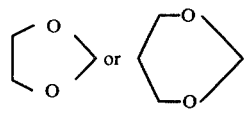

However, attempts to ring-close an $-N,N$-di($\beta$-hydroxyethyl) moiety employing this reaction have been unsuccessful.

E. V. Dehmlow and J. Schmidt, Tetrahedron Lett., No. 2, p. 95 (1976) have reported that dichloromethane reacts with alkylOH and arylOH in the presence of solid potassium hydroxide and a quaternary ammonium salt to form the corresponding di(alkoxy)methanes and di(aryloxy)methanes as illustrated below.

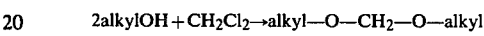

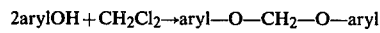

Quite unexpectedly, it has been found that this reaction can be applied to an $-N,N$-di($\beta$-hydroxyethyl) moiety to yield a cyclic product rather than a polymeric product.

In one aspect, the present invention is concerned with the reaction of a dihalomethane and compounds possessing an $-N,N$-di($\beta$-hydroxyethyl) substituent to protect the hydroxy groups by the formation of a cyclic moiety compatible with and stable in the presence of organometallic reagents. In another aspect, the present invention is concerned with the ring-closed products thus formed.

SUMMARY OF THE INVENTION

It is, therefore, the primary object of the present invention to provide novel compounds possessing a tetrahydro-2H,4H-1,3,6-dioxazocino moiety.

It is another object of the present invention to provide a method of synthesizing said compounds.

Other objects of this invention will in part be obvious and will in part appear hereinafter.

The invention accordingly comprises the process involving the several steps and the relation and order of such steps with respect to each of the others and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

According to the present invention, it has been found that the $-N,N$-di($\beta$-hydroxyethyl) substituent of compounds, $RN(CH_2CH_2OH)_2$, may be converted to an 8-membered cyclic moiety, i.e., a tetrahydro-2H,4H-1,3,6-dioxazocino moiety by reaction with certain dihalomethanes in the presence of a quaternary ammonium salt and a solid alkali metal hydroxide or concentrated aqueous solution thereof. This reaction is illustrated below wherein R represents phenyl.

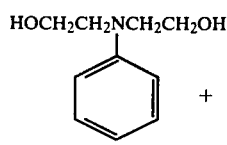

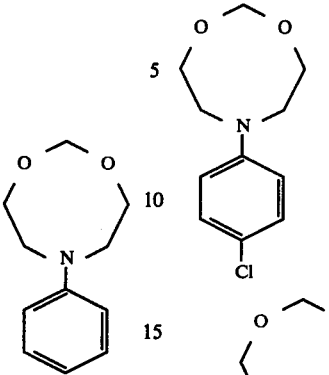

The dioxazocino moiety thus formed is stable in the presence of organometallic reagents yet capable of being reopened under relatively mild conditions to regenerate the original —N,N-di($\beta$-hydroxyethyl) group, if desired.

The novel compounds of the present invention produced according to the novel process described above and their corresponding Grignard and lithium reagents may be represented by the formula:

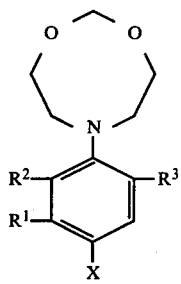

wherein $R^1$ and $R^2$ taken individually each are hydrogen, alkoxy or alkyl and taken together represent the carbon atoms necessary to complete a fused benzene ring, $R^3$ is hydrogen, alkoxy or alkyl and X represents hydrogen, chloro, bromo, iodo, Li, MgCl, MgBr or MgI. Preferably, the alkyl groups and the alkoxy groups comprising $R^1$, $R^2$ and $R^3$ are lower alkyl having 1 to 4 carbon atoms and lower alkoxy having 1 to 4 carbon atoms. Usually, $R^1$ and $R^2$ are hydrogen or a fused benzene ring and $R^3$ is hydrogen.

Specific examples of compounds possessing a tetrahydro-2H,4H-1,3,6-dioxazocino moiety within the scope of the present invention are as follows:

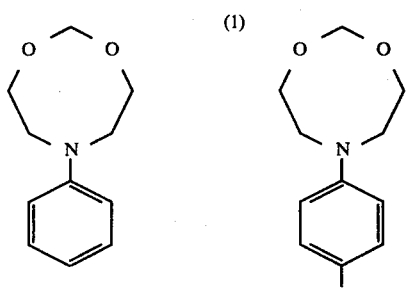

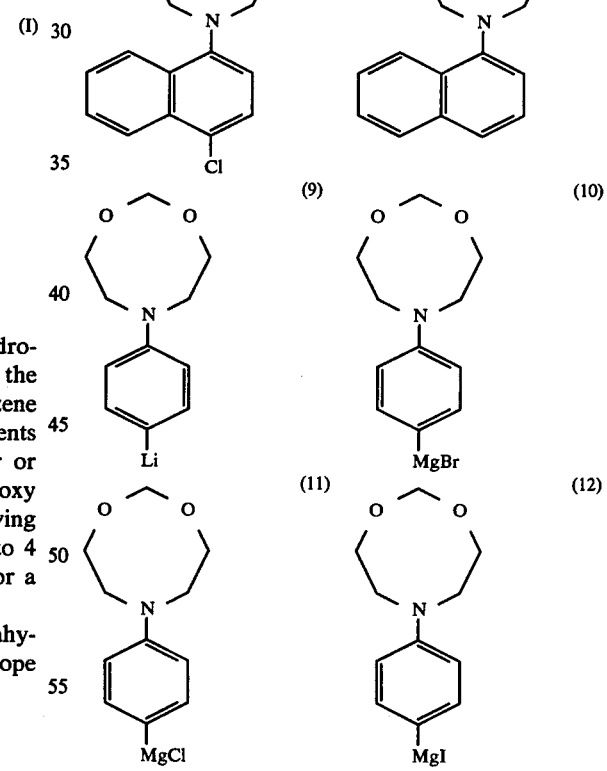

The compounds of formula I wherein X is hydrogen, chloro, bromo or iodo may be prepared by reacting the selected N,N-di($\beta$-hydroxyethyl)aniline or the 4-chloro, bromo or iodo derivatives thereof with at least 1 molar equivalent of a dihalomethane selected from dichloromethane and dibromomethane in the presence of a quaternary ammonium salt and solid sodium or potassium hydroxide or concentrated, i.e., 25% by weight aqueous solution thereof. The starting compound is reacted with an excess of the said dihalomethane, and since the dihalomethane is employed as the solvent for the reaction, it is usually present in a large excess. The amount of hydroxide also may vary over a broad range. At least about 1 equivalent is used as based on 1 equivalent of starting compound, but ordinarily, a large excess of hydroxide is used to increase the rate of reaction. The quaternary ammonium salt is employed in an amount sufficient to catalyze the reaction, generally an amount between about 0.5 and 5.0 equivalents based on 1 equivalent of starting compound. The reaction may be conducted at a temperature between about 25° C. and reflux temperature of the dihalomethane and is conveniently carried out at room temperature, i.e., about 25° C.

The quaternary ammonium salt may be any of those commonly used as phase-transfer catalysts and usually is a tetraalkylammonium bromide or chloride containing up to about 20 carbon atoms in each alkyl group, such as, n-tetrabutylammonium bromide, tetrahexylammonium chloride, ethylhexadecyldimethylammonium bromide, benzyltriethylammonium chloride, dodecyltrimethylammonium bromide and trioctylpropylammonium chloride.

The following examples are given to further illustrate the present invention and are not intended to limit the scope thereof.

EXAMPLE 1

Preparation of the compound of the formula (2):

To 5.0 g. of powdered potassium hydroxide was added 150 ml. of dichloromethane. The mixture was stirred vigorously and then 6.5 g. of p-bromo-N,N-bis-(beta-hydroxyethyl)aniline was added followed by adding 3.5 g. of tetra-n-butylammonium chloride.2H$_2$O. The resulting reaction mixture was refluxed overnight while stirring vigorously. By morning, the powdered potassium hydroxide had become fused, and the reaction mixture was clear and colorless. TLC analysis indicated that the reaction was not complete. Additional powdered potassium hydroxide (14.4 g.) and tetra-n-butylammonium chloride.H$_2$O (3.5 g.) was added to the reaction mixture. After an initial exotherm had subsided, the mixture was heated at reflux for about 20 hours. TLC analysis indicated the absence of starting aniline. The reaction mixture was then cooled, decanted from the solid-tacky potassium hydroxide, washed with four portions of fresh water and dried over anhydrous calcium sulfate. The solvent was removed under reduced pressure to give a colorless oil. Some of the oil was distilled at 0.015 mm Hg in an oil bath having a temperature between about 218°–230° C. giving a colorless oil (boiling point 142° C.) which solidified upon standing to give the title compound.

EXAMPLE 2

Preparation of the compound of formula (2):

To approximately 1 l. of dichloromethane was added 111.0 g. of p-bromo-N,N-($\beta$-hydroxyethyl)aniline followed by the addition of 125.0 g. of crushed potassium hydroxide and 25.0 g. of n-tetrabutylammonium bromide with vigorous stirring. The reaction mixture was then stirred overnight in an ice water bath. (The reaction tends to be exothermic in the first 2-3 hours.) Next morning some starting material remained and the mixture was then stirred at room temperature for 24 hours. The organic portion was then decanted, washed with several portions of fresh water and dried over anhydrous sodium sulfate. The solvent was removed under reduced pressure leaving a colorless oil which was distilled under vacuum at approximately 0.05 to 0.08 mm Hg, boiling range 143°–149° C. The colorless oil that was collected quickly became solid. The resulting solid was redissolved in a small amount of dichloromethane and precipitated with petroleum ether to yield 22.0 g. of the title compound.

EXAMPLE 3

Preparation of the compound of formula (2):

1 g. of p-bromo-N,N-bis($\beta$-hydroxyethyl)aniline was dissolved in 20 ml. of dibromomethane. To this solution was added about 20 ml. of 25% aqueous sodium hydroxide solution followed by the addition of about 0.7 g. of trioctylpropylammonium chloride. The reaction mixture was then refluxed with stirring for 2 hours. TLC on silica gel with ether showed product but no remaining starting material. The organic layer was separated, washed with water, dried over anhydrous sodium sulfate and evaporated to leave an oil (approximately 0.8 g.). The oil was dissolved in a 7/3 mixture of dichloromethane and petroleum ether, placed on a column of silica gel and eluted first with the 7/3 solvent mixture and then with dichlormethane alone. The product which eluted with the dichloromethane was collected and evaporated leaving an oil that crystallized to give about 300 mg. of the title compound as an off-white solid.

EXAMPLE 4

Preparation of the compound of formula (9):

To 125 mls. of dry tetrahydrofuran was added 4.8 g. of N-(p-bromophenyl)tetrahydro-2H,4H-1,3,6-dioxazocine (the compound of formula 2). The resulting solution was stirred under nitrogen and cooled to −70° C. 7.32 ml. of n-butyllithium (2.4 M in hexane) was slowly added dropwise to the cooled solution, and then the reaction mixture was stirred at −70° C. for 45 minutes. Rather than isolating the 4-lithium derivative from the tetrahydrofuran-hexane solution, the solution of lithium derivative ordinarily is used directly in the synthesis of the compounds of aforementioned application Ser. No. 836,008.

As mentioned above, the tetrahydro-2H,4H-1,3,6-dioxazocino moiety may be opened under comparatively mild conditions to regenerate the di-N,N-($\beta$-hydroxyethyl) group. This may be accomplished by treating with weak acid. For example, the dioxazocino ring was opened as follows:

A portion of the compound of Example 1 was suspended in water, and about 6–8 drops of conc. HCl was added. The suspension was heated on a steam bath to dissolve the solids and then further heated for about 2 hours, cooled and neutralized with potassium carbonate. A white suspension was obtained which was extracted with dichloromethane. Silica gel TLC (60:40 ethyl acetate-hexane) of the extract gave one spot, and the spot was identical to p-bromo-N,N-bis-($\beta$-hydroxyethyl)aniline, the starting material of Example 1.

As a further illustration of regenerating the —N,N-di($\beta$-hydroxyethyl) moiety from the tetrahydro-2H,4H-1,3,6-dioxazocino moiety, 8.6 g. of compound A having the formula

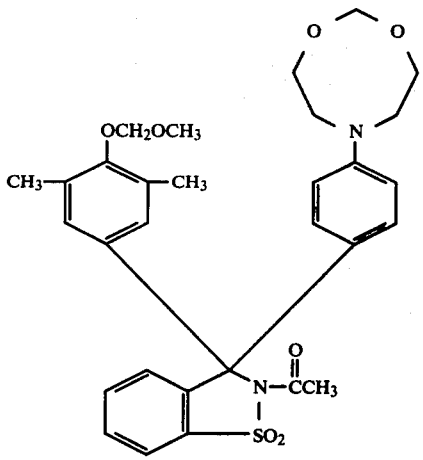

was suspended in approximately 30–35 ml. of anhydrous trifluoroacetic acid and stirred vigorously while cooling in a very cold water bath. The suspension was diluted with 170 mls. of dichloromethane and then stirred in a cold water bath for 30–40 minutes. After further dilution with more dichloromethane, the suspension was washed with 3 portions of saturated aqueous sodium acetate solution. (The magenta color disappeared giving a light yellow-orange color.) It was then washed with fresh water and dried over anhydrous sodium sulfate. The solvent was removed leaving a pink solid (Compound B) which was dried in vacuo in the presence of $P_2O_5$.

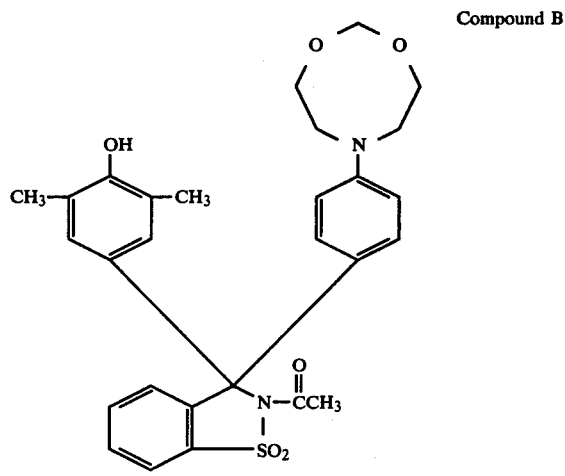

Compound B 0.5 g. of Compound B was dissolved in 15 ml. of trifluoroacetic acid. The resulting solution was diluted with 15 ml. of water and heated on a steam bath for about 2½ hours until all of the starting material had disappeared as determined by TLC on silica gel using 60:40 ethyl acetate-petroleum ether. 125 ml. of dichloromethane was added to the aqueous reaction solution, and the mixture was washed with several portions of saturated sodium acetate solution. (The intense magenta-violet color disappeared giving an almost colorless mixture.) The organic portion was decanted, washed with several portions of fresh water and dried over anhydrous sodium sulfate. Upon removal of the solvent, Compound C was obtained as a fluffy, light pink solid which was dried in vacuo. Yield 0.26 g.

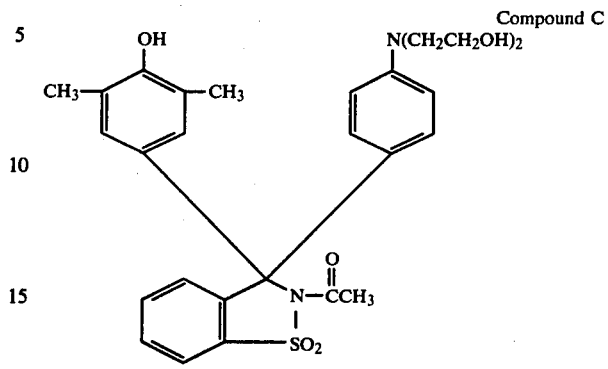

Compound C

The subject compounds are useful in the synthesis of certain 3,3-disubstituted-2,3-dihydrobenz[d]isothiazole-1,1-dioxide dyes possessing a carbonyl group in the 2-position which dyes, as noted above, may be used as pH-sensitive indicator dyes, antihalo dyes or photographic optical filter agents depending upon the 3,3 substituents and the carbonyl group. In synthesizing these dyes, the subject lithium derivatives may be reacted with a 3-(4'-OP-1'-phenyl/4'-OP-1'-naphthyl)-benz[d]isothiazole-1,1-dioxide as described in aforementioned U.S. patent application Ser. No. 836,008 or a lithium derivative of a blocked phenol or a blocked 1-naphthol may be reacted with a 3-[4'-(tetrahydro-2H,4H-1,3,6-dioxazocino)phenyl/naphthyl]-benz[d]isothiazole-1,1-dioxide as described in copending U.S. patent application Ser. No. 836,025 of Alan L. Borror, James W. Foley, Marcis M. Kampe and John W. Lee, Jr. filed concurrently herewith to give in both cases a 3,3-disubstituted-2,3-dihydrobenz[d]isothiazole-1,1-dioxide wherein one of the 3,3 substituents is a (4'-OP-1'-phenyl/4'-OP-1'-naphthyl) moiety and the other of the 3,3 substituents is a phenyl or naphthyl moiety substituted in the 4'-position with a tetrahydro-2H,4H-1,3,6-dioxazocino moiety. The 3,3-disubstituted intermediate obtained is then reacted with the selected carboxylic acid halide to give the corresponding 2-carbonyl derivative followed by removal of the protecting group used to block the phenol (or 1-naphthol). After removing the protecting group from the phenol (or 1-naphthol), the dioxazocino moiety may be opened to regenerate the bis-($\beta$-hydroxyethyl) moiety if desired.

The aforementioned 3-[4'-tetrahydro-2H,4H-1,3,6-dioxazocino)phenyl/naphthyl]-benz[d]isothiazole-1,1-dioxides may be prepared by reacting a lithium-substituted compound of the present invention with the N-lithium salt of saccharin or by reacting a Grignard compound of the present invention with saccharin pseudo-chloride. The lithium derivatives may be prepared by reacting a halo-substituted compound of the present invention with lithium metal or with n-butyllithium. The halo substituent may be chloro, bromo or iodo when lithium metal is employed and is either bromo or iodo when a lithium exchange reaction is employed. The Grignard derivatives may be prepared by reacting a halo-substituted compound of the present invention with magnesium metal to give the corresponding magnesium halide. Where X in formula I is hydrogen, the corresponding halo derivatives may be synthesized by reaction with, for example, chlorine or bromine with or without a catalyst, N-bromosuccinimide or iodinemonochloride. The said dioxazocinophenyl-/naphthyl-benz[d]isothiazole-1,1-dioxides prepared from the subject compounds form the subject matter of copending U.S. patent application Ser. No. 836,022 of Alan L. Borror, James W. Foley and John W. Lee, Jr. filed concurrently herewith, which application for convenience is incorporated herein.

As mentioned above, the compounds of the present invention are useful as intermediates in the synthesis of certain 3,3-disubstituted-2,3-dihydrobenz[d]isothiazole-1,1-dioxides possessing a carbonyl group in the 2-position. Such compounds possessing a 4'-hydroxyphenyl moiety as one of the 3,3 substituents and a phenyl-/naphthyl or 4'-substituted phenyl/4'-substituted naphthyl moiety as the other of the 3,3 substituents form the subject matter of copending U.S. patent application Ser. No. 836,021 of Stanley M. Bloom, Alan L. Borror and James W. Foley filed concurrently herewith and of copending U.S. patent application Ser. Nos. 835,998, 836,005 and 836,009 of Stanley M. Bloom of Alan L. Borror and James W. Foley also filed concurrently herewith. As discussed in the aforementioned applications, compounds may be selected for use as classical pH-sensitive indicator dyes or as photographic optical filter agents and filter agent precursors depending upon the 2-substituent of the benz[d]isothiazole ring. The photographic use of those compounds which may be employed as photographic optical filter agents and filter agent precursors forms the subject matter of copending U.S. patent application Ser. No. 836,006 of Stanley M. Bloom, Alan L. Borror and James W. Foley filed concurrently herewith. The 2,3-dihydrobenz[d]isothiazole-1,1-dioxides possessing a 4'-hydroxynaphthyl moiety as one of the 3,3 substituents and a naphthyl or 4'-substituted naphthyl moiety as the other of the 3,3 substituents form the subject matter of copending U.S. patent application Ser. No. 836,067 of Alan L. Borror, Louis Cincotta, Ernest W. Ellis and James W. Foley filed concurrently herewith, and as described therein, compounds may be selected for use as classical pH-sensitive indicator dyes or as antihalo dyes in photography.

Since certain changes may be made in the above processes and products without departing from the scope of the invention herein involved, it is intended that all matter contained in the above description shall be interpreted as illustrative and not in a limiting sense.

What is claimed is:

1. A compound of the formula

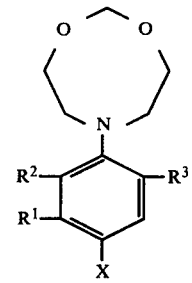

wherein $R^1$ and $R^2$ taken individually each are hydrogen, alkoxy or alkyl and taken together represent the carbon atoms necessary to complete a fused benzene ring, $R^3$ is hydrogen, alkoxy or alkyl and X represents chloro, bromo or iodo.

2. A compound as defined in claim 1 wherein X is chloro.

3. A compound as defined in claim 1 wherein X is bromo.

4. A compound as defined in claim 1 wherein X is iodo.

5. A compound as defined in claim 1 wherein $R^1$ and $R^2$ each are hydrogen.

6. A compound as defined in claim 1 wherein $R^1$ and $R^2$ taken together represent the carbon atoms necessary to complete a fused benzene ring.

7. A compound as defined in claim 5 wherein $R^3$ is hydrogen.

8. A compound as defined in claim 6 wherein $R^3$ is hydrogen.

9. A compound as defined in claim 7 wherein X is bromo.

* * * * *